United States Patent [19]

Walder et al.

[11] Patent Number: 5,403,711
[45] Date of Patent: Apr. 4, 1995

[54] NUCLEIC ACID HYBRIDIZATION AND AMPLIFICATION METHOD FOR DETECTION OF SPECIFIC SEQUENCES IN WHICH A COMPLEMENTARY LABELED NUCLEIC ACID PROBE IS CLEAVED

[75] Inventors: Joseph A. Walder; Roxanne Y. Walder, both of Iowa City, Iowa

[73] Assignee: University of Iowa Research Foundation, Iowa City, Iowa

[21] Appl. No.: 88,622

[22] Filed: Jul. 6, 1993

Related U.S. Application Data

[63] Continuation of Ser. No. 757,555, Sep. 11, 1991, abandoned, which is a continuation of Ser. No. 173,127, Mar. 24, 1988, abandoned, which is a continuation-in-part of Ser. No. 126,564, Nov. 30, 1987, abandoned.

[51] Int. Cl.$^6$ .................... C12Q 1/68; C07H 21/04; C12P 19/34
[52] U.S. Cl. ........................ 435/6; 536/24.3; 435/91.2
[58] Field of Search ............ 536/24.3; 435/91.2

[56] References Cited

U.S. PATENT DOCUMENTS

| | | | |
|---|---|---|---|
| 4,511,713 | 4/1985 | Miller et al. | 536/27 |
| 4,554,088 | 11/1985 | Whitehead et al. | 252/62.54 |
| 4,775,619 | 10/1988 | Urdea | 435/6 |
| 4,876,187 | 10/1989 | Duck et al. | 435/6 |
| 5,011,769 | 4/1991 | Duck et al. | 435/6 |

OTHER PUBLICATIONS

Bonner *Methods in Enzymology* 152 Academic Press New York, N.Y. pp. 55–61 (1986).
Sisodia et al Nuc Acids Res 15(5): 1995–2011 (1987).
Taylor et al Nuc Acids Res 13(24): 8749–8764.
Maniatis et al *Molec Cloning* Cold Spring Harbor Press CSH N.Y. pp. 188–189, 230–233 1982.
Zoon Methods in Enzymology 152 Academic Press New York N.Y. pp. 25–29 1986.

*Primary Examiner*—Mindy B. Fleisher
*Attorney, Agent, or Firm*—Seed and Berry

[57] ABSTRACT

A method of detection of nucleic acid (DNA or RNA) target sequence in which such a sequence serves as a cofactor for a catalytic reaction in which a complementary, labeled nucleic acid probe is cleaved such that the target sequence is released intact and can repeatedly recycle through the reaction pathway, thereby providing signal amplification.

30 Claims, 6 Drawing Sheets

DETECTION OF A SPECIFIC DNA SEQUENCE USING THE CHA METHOD (1) Denaturation of Double-Stranded Target DNA Molecule (2) Addition Of Excess Labeled Nucleic Acid Probe And Enzyme Or Other Catalyst To Cleave Probe Once Hybridized To Target DNA Sequence (3) Hybridization Of The Probe To Target DNA Strand (4) Cleavage Of The Probe And Recycling Of The Target DNA Molecule (5) Measurement Of Labeled Probe Cleavage Product After Repeated CHA Cycles

STANDARD STOICHIOMETRIC HYBRIDIZATION ASSAY TO DETECT DNA SEQUENCES
(1) Isolate Sample DNA
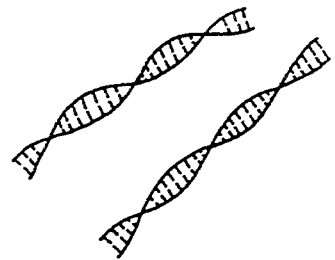
(2) Immobilize Denatured (Single-Stranded) DNA On A Solid Support
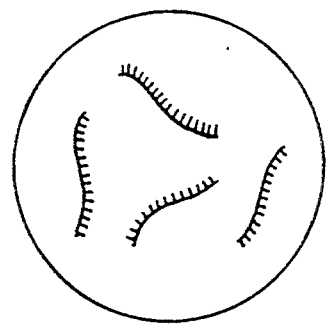
Labeled Probe
(3) Hybridize With Labeled Probe
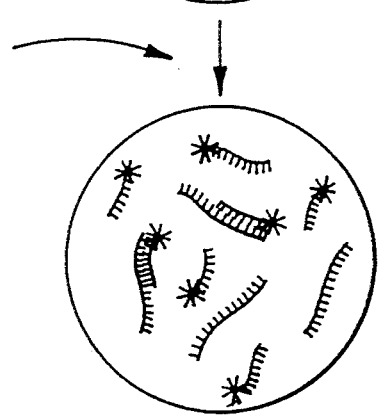
(4) Wash Out Probe Nonspecifically Bound And Detect Signal
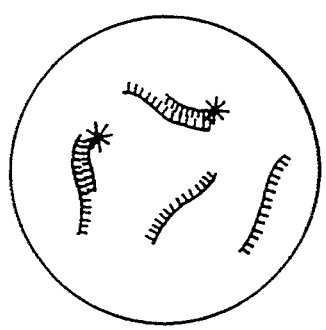
FIG.1

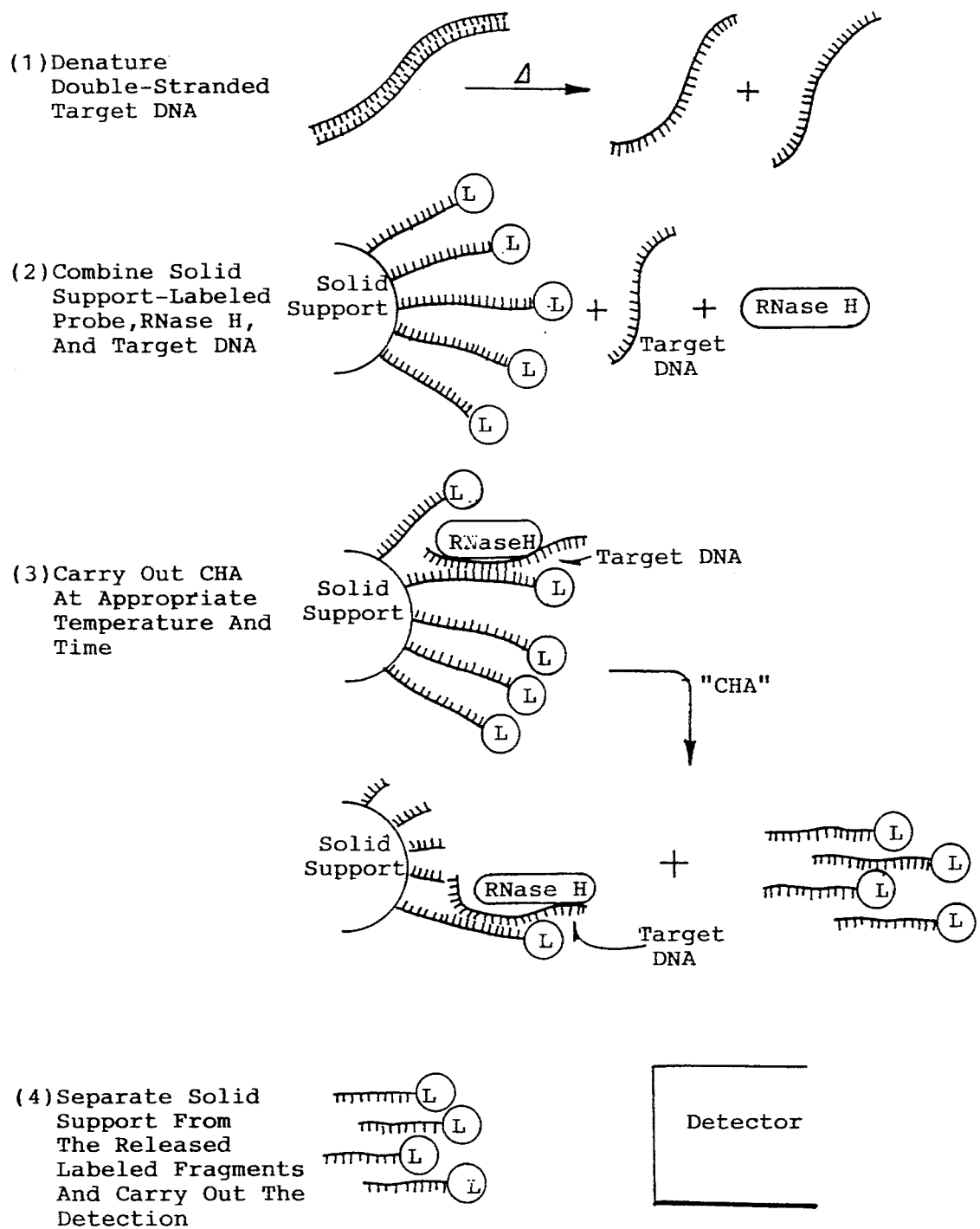

EXPONENTIAL CATALYTIC HYBRIDIZATION AMPLIFICATION SYSTEM (1) Denaturation of Sample DNA To Form Single-Stranded Species. Unique Target Sequence is Represented by (T).

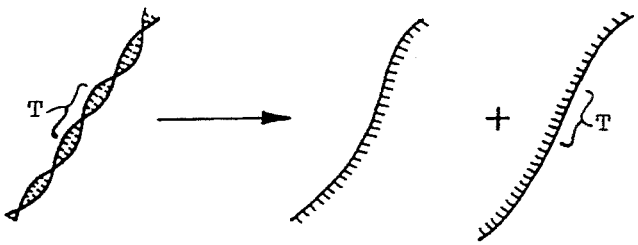

(2) Addition of Target DNA and RNase H to Solid Support System I And II. Solid Support I Contains Probe With Complementary Cleavable (T') and (X) Sequence. Solid Support II Contains Complementary Cleavable (X') and Labeled (T) Sequence.

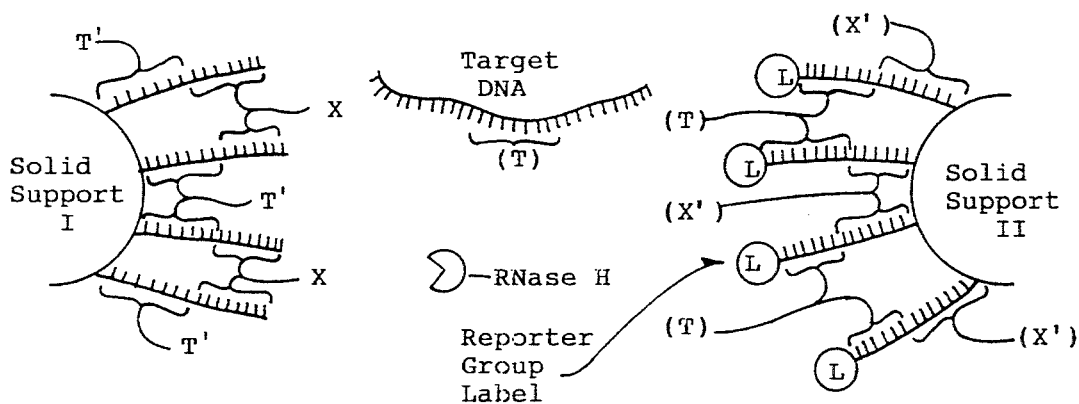

(3) Target DNA Sequence (T) Hybridizes To Complementary Cleavable (T') On Solid Support I.

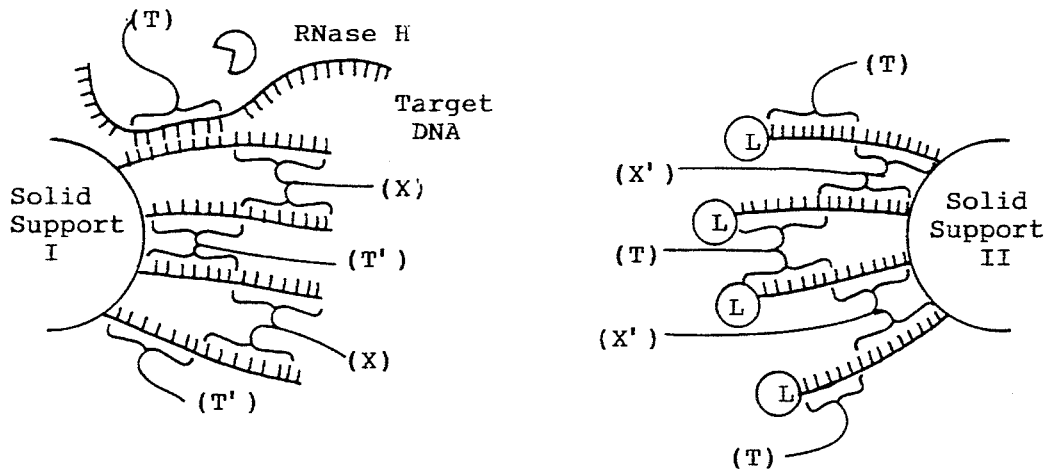

FIG.4A (4) Cleavage Of (T') Releases Sequence (X) Which Diffuses To Solid Support II, Hybridizes to Complementary Cleavable Sequence (X') and Releases a Labeled (T) Sequence. Original Target Sequence (T) Continues To Release More (X) Sequences.

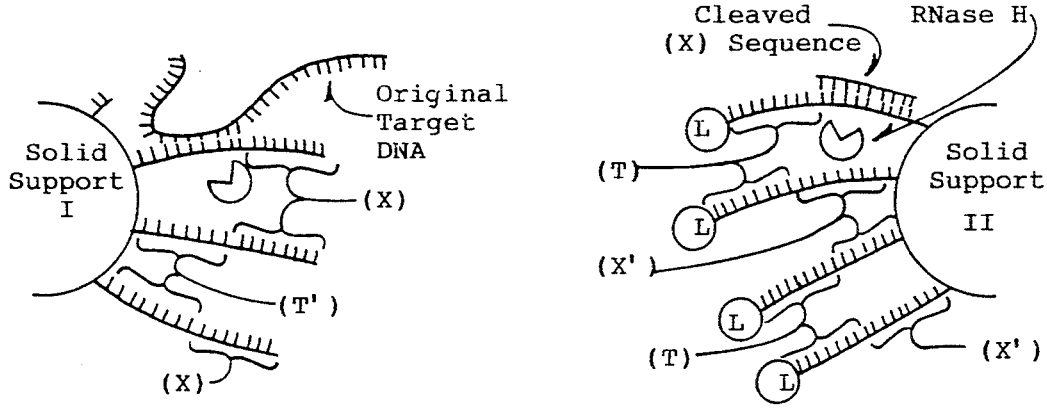

(5) Labeled (T) Sequence diffuses back to Solid Support I, hybridizes with Cleavable (T'), and releases more (X) Sequences.

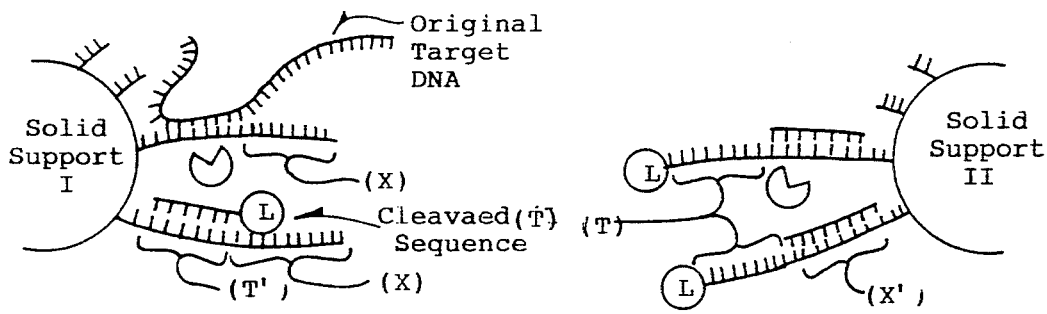

(6) CHA process continues between the two Solid Support Systems with the exponential release from Solid Support II of Labeled Probes for subsequent Detection.

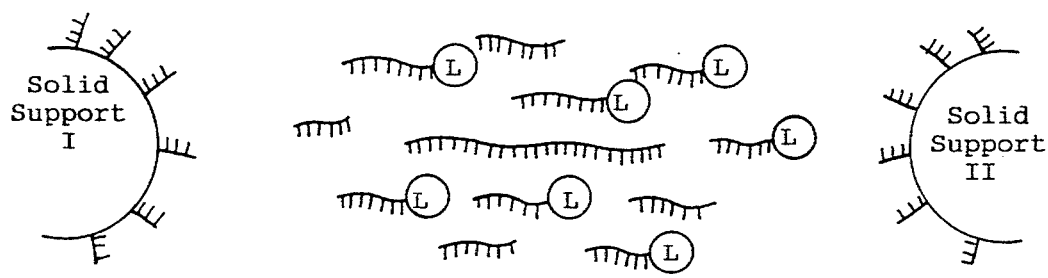

FIG.4B

DETECTION OF SPECIFIC RNA SEQUENCES USING A COMPETITIVE CHA ASSAY
Add Complementary DNA Molecule to Test Sample of RNA, Hybridize then add Labeled RNA Probe and RNase H:
Sample RNA (?)    DNA Molecule    Labeled RNA
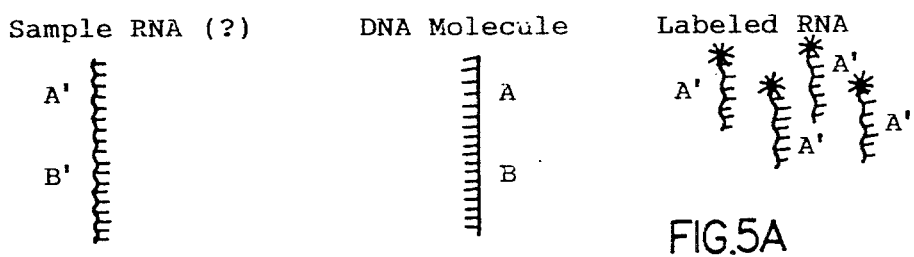
FIG.5A
Sample "Does"
Contain Target
RNA Sequence
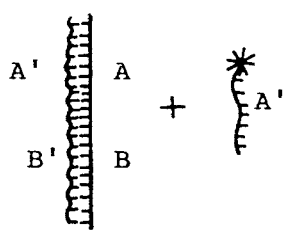
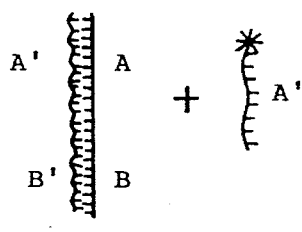
No Labeled Fragments
Released
FIG.5B
Sample "Does Not"
Contain Target
RNA Sequence
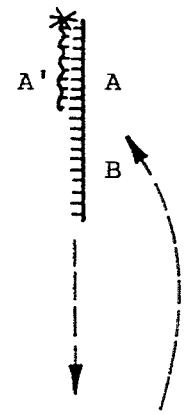
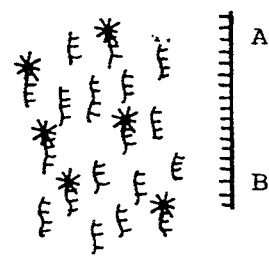
Labeled Fragments
Released
FIG.5C

NUCLEIC ACID HYBRIDIZATION AND AMPLIFICATION METHOD FOR DETECTION OF SPECIFIC SEQUENCES IN WHICH A COMPLEMENTARY LABELED NUCLEIC ACID PROBE IS CLEAVED

GRANT REFERENCE

The invention described herein was made in part in course of work under grants from the National Institutes of Health, Grant Nos. HL-33555 and AM-25295.

CROSS-REFERENCE TO RELATED APPLICATION

This application is a continuation of U. S. patent application Ser. No. 07/757,555, filed Sep. 11, 1991, now abandoned, which is a continuation of U.S. patent application Ser. No. 07/173,127, filed Mar. 24, 1988, now abandoned, which is a continuation-in-part of U.S. patent application Ser. No. 07/126,564, Filed Nov. 30, 1987, now abandoned.

BACKGROUND OF THE INVENTION

1. Field of the Invention

This invention provides a diagnostic assay methodology for the sensitive detection of specific nucleic acid (DNA and RNA) sequences in biological and clinical samples. The invention particularly addresses the problem of detecting low copy numbers of a target sequence with high specificity.

All current methods for the detection of DNA and RNA are based on the stoichiometric (1:1) hybridization of a complementary, labeled nucleic acid probe to the target sequence (see FIG. 1). The present invention is a marked departure from this approach: the target sequence serves as a cofactor for a reaction in which the probe is cleaved catalytically. After cleavage of the probe, the target sequence is released intact and can be repeatedly recycled through the reaction leading to a large amplification of the response (see FIG. 2). We have termed such reaction schemes catalytic hybridization amplification reactions. In such assays, cleavage of the labeled probe signals the presence of the target sequence. The sensitivity of the method is far greater than existing procedures, all of which are based on stoichiometric or unitary hybridization schemes in which the target sequence captures one, and only one, molecule of the probe. Several embodiments of the catalytic hybridization amplification method are described below. All operations required for such assays are simple and can be readily carried out in a clinical laboratory. The invention will have applications in the diagnosis of a variety of diseases in man and other species including genetic disorders, infectious diseases, and cancer.

2. Description of Prior Art

It is well known that nucleic acids, i.e., deoxyribonucleic acids (DNA) and ribonucleic acids (RNA) are essential building blocks of all organisms. These are high molecular weight polymers that are made up of many nucleotide units, each such nucleotide unit being composed of a base (a purine or a pyrimidine), a sugar (which is either ribose or deoxyribose) and a molecule of phosphoric acid. DNA contains deoxyribose as the sugar moiety and the bases adenine, guanine, cytosine, and thymine (which may be represented as A, G, C and T, respectively). RNA contains ribose instead of deoxyribose and uracil (U) instead of thymine.

The nucleotide units in DNA and RNA are assembled in definite linear sequences which determine specific biological functions, In bacterial cells, and in all higher species, DNA directs its own replication, and also serves as the template for the synthesis of RNA molecules whose nucleotide sequences carry the information encoded by the DNA. The process of RNA synthesis is termed transcription. RNA molecules serve several different functions within the cell. Messenger RNAs (mRNAs) direct protein synthesis. Ribosomal RNAs (rRNAs) are important constituents of ribosomes, the organelle within the cell at which mRNAs are read, or translated, and proteins are made.

Collectively, the genetic information of an organism is termed the genome. The genome of bacteria and all higher species is composed of DNA. The genome of viruses may be either DNA or RNA. In any case, the genome of any particular species, whether a virus, bacteria or a higher organism has a characteristic nucleotide sequence which, stated simply, can be viewed as the "fingerprint" of that species. Sequences within a genome that code for proteins, or that are transcribed to form RNAs with specific functions such as ribosomal RNA represent individual genes. Small viruses such as the AIDS virus have as few as 10 genes. The human genome contains approximately 50,000 genes.

According to the well known Watson-Crick model, DNA molecules consist of two polynucleotide strands coiled about a common axis. The resulting double helix is held together by hydrogen bonds between complementary base pairs in each strand. Hydrogen bonds are formed only between adenine (A) and thymine (T) and between guanine (G) and cytosine (C). Hence within the double helix, adenine (A) and thymine (T) are viewed as complementary bases which bind to each other as A—T. The same is true for guanine (G) and cytosine (C) as G—C.

In a single polynucleotide chain, any sequence of nucleotides is possible. However, once the order of bases within one strand of a DNA molecule is specified, the exact sequence of the other strand is simultaneously determined due to the indicated rules of base pairing. Accordingly, each strand of a DNA molecule is the complement of the other. The process by which two complementary DNA strands associate with one another is termed hybridization. The process of strand separation, which is generally accomplished by heating the sample, is termed melting or denaturation of the duplex. Duplexes have a characteristic melting temperature (Tm) depending primarily on length, composition, and salt concentration. The following equation provides a useful approximation of the Tm:

$$Tm = 16.6 \times \log Cs + 0.41 \times (\% \ G+C) + 81.5 - 820/L \quad (1)$$

where $Cs$ is the salt concentration, ($\% \ G+C$) is the percent G-C content, and L is the length of the duplex (Schildkraut C. and Lifson, S. (1965) Biopolymers 3, 195–208; and Thomas, C. A. Jr. and Dancis, B. M. (1973) Journal of Molecular Biology 77, 43–55). Mismatches between the two strands of a duplex (e.g. a C-T base pair) can occur, but decrease the stability of the helix significantly and lower the melting temperature.

In addition to DNA:DNA duplexes, DNA:RNA duplexes and RNA:RNA duplexes can also form and occur naturally. DNA:RNA duplexes are formed transiently in the process of transcription in which DNA serves as a template for RNA synthesis. RNA:RNA duplexes occur as the genetic material of certain viruses and are also formed in so-called hairpin loops of ribosomal RNA and transfer RNA. In duplexes involving an RNA strand, uracil (U) pairs with adenine (A). Within a single polynucleotide strand, sequences of both RNA and DNA can also occur. Such RNA-DNA copolymers are formed as intermediates in the replication of DNA. The melting temperature of a DNA:RNA or an RNA:RNA duplex may differ somewhat, depending on solution conditions, from that of a DNA:DNA duplex of the same sequence, but the equation given above remains a useful approximation of the Tm. For a further discussion of these various polynucleotide structures and their biological functions see "Genes III" by Benjamin Lewin, John Wiley and Sons, 1987, which is incorporated herein by reference.

Recent advances in molecular biology employing recombinant DNA techniques have led to new diagnostic and therapeutic strategies. In the area of DNA probe diagnostics, DNA probes are used to detect the presence of a complementary target nucleic acid sequence in the sample. Applications include the diagnosis of infectious diseases, cancer and genetic disorders. In the case of infectious diseases, the target can be a DNA or RNA sequence unique to a particular bacteria or virus.

In certain cancer cells there are specific gene rearrangements which can be detected, e.g. the translocation of the c-abl oncogene in chronic myelogenous leukemia. Genetic defects can involve large deletions or insertions of DNA, or a single point mutation as in the case of sickle cell disease. In the latter case, it is necessary to detect the alteration of a single base pair in the context of flanking sequences that are identical to those found in the normal gene.

All nucleic acid diagnostic assays involve three fundamental steps:

(1) Isolation and further preparation of DNA or RNA from the sample.

When DNA is isolated it is generally sheared by mechanical forces. With gentle manipulation, the largest fragment size may be up to about 100,000 base pairs. DNA may also be purposefully cut with sequence specific endonucleases termed restriction enzymes to give rise to fragments of discrete sizes. Such is the case in so-called Southern blot analysis in which the fragments are subsequently separated according to size by electrophoresis and then immobilized on a filter such as nitrocellulose or a nylon membrane (Southern, E. M. (1975) Journal of Molecular Biology 98, 503–517).

(2) Hybridization of a complementary, labeled nucleic acid probe to the target sequence.

In this process, the sample is denatured, generally by heating, to ensure that the target sequence is single stranded. The labeled probe is then allowed to hybridize to the target. Molecules of the probe that are weakly bound to other sequences within the sample, or the filter on which it is immobilized, are then washed away. To achieve adequate specificity, the melting temperature of the probe:target duplex must be at least 5 to 10 degrees above that of duplexes that may be formed between the probe and other sequences present within the sample with which there is one or more mismatches.

(3) Detection of the amount of the labeled probe hybridized to the DNA or RNA within the sample.

Suitable reporter groups with which the probe may be labeled include radioisoopes such as $^3H$, $^{32}p$ or $^{121}I$, fluorescent dyes such as fluorescene, Texas Red or the phycobiliproteins, or enzyme markers such as alkaline phosphatase, $\beta$-galactosidase, glucose oxidase or peroxidases. An example of a diagnostic assay in which the sample nucleic acid is immobilized on a filter is shown in FIG. 1 (see Falkow et al. (1982) U.S. Pat. No. 4,358,535).

In addition to the filter format, a variety of other strategies for diagnostic hybridization assays have been described, see for example Heller et al. (1983) EPA 0 070 685 and EPA 0 707 687; Rentz, M. and Kurz, C. (1984) Nucleic Acids Research, 12, 3435–3444; Ruth, J. L. (1984) P.C.T. W084/03285; and Kohne, D. (1984) P.C.T. W084/02721. In each of these systems the reporter group that is to be detected is attached directly to the probe as is shown in FIG. 1. Alternatively, an indirect labelling scheme may be employed. In the method described by P. Kourlisky et al. (1979) GB 2 019 408 the probe is labeled with biotin. After the probe is hybridized to the target sequence, a complex of the enzyme $\beta$-galactosidase covalently linked to the protein avidin is added to the sample. Avidin binds specifically and with very high affinity to the biotin label attached to the probe. The probe:target duplex is then detected by providing an appropriate substrate for $\beta$-galactosidase which is hydrolyzed to give a fluorescent or colored product. Biotin-avidin probe systems have also been described by Ward et al. (1982) EPA 0 063 879, and by Engelhardt et al. (1984) EPA 0 097 373. More recently, Carrico (1987) EPA 0 209 702 have described an indirect labelling strategy in which a probe:target duplex formed between an RNA strand and a DNA strand are detected using an antibody which binds specifically to RNA:DNA duplexes.

All of the above prior art methods involve a stoichiometric or unitary hybridization reaction in which the target sequence binds to or captures one and only one molecule of the probe. The present invention provides a novel and improved hybridization assay method in which the target sequence is able to capture many molecules of the probe in a repeating series of reactions. This is accomplished by cleavage of the probe within the probe:target duplex such that the target sequence is released intact and can repeatedly recycle through the reaction pathway. We term such methods catalytic hybridization amplification (CHA) reactions. A generalized version of the CHA method is shown in FIG. 2. In such assays, the signal that is detected results from the cleavage of the probe. The sensitivity of the method is far greater than that of earlier hybridization schemes, all of which are based on a stoichiometric, i.e. 1:1, association between the target sequence and the probe.

Several methods described previously involve cleavage of the probe used in the hybridization assay, but preclude recycling of the target sequence, the essential element of the present invention. Thus, Ashihara et al. (1985) EPA 0 142 299 describe a method in which the DNA:DNA duplex formed between the probe and the target sequence is cleaved by a restriction enzyme. The restriction enzyme recognizes a specific sequence, generally 4 to 6 base pairs in length, within the duplex and cleaves both the probe and the target strand. Because the target is cleaved, it is impossible for it to recycle through the reaction pathway. A procedure for detecting single base changes, i.e. point mutations, within DNA has been described by Myers et al. (1985) Science 230, 1242–1246 that is based on the cleavage of an RNA probe. A labeled RNA probe is first hybridized to the target DNA. The RNA probe hybridized to the DNA is then subjected to cleavage by the enzyme RNaseA. Excess, unbound molecules of the probe are fully degraded. If the RNA forms a perfect duplex with no base pair mismatches with the DNA, the hybridized RNA strand will not be cut. If there are one or more base pair mismatches, the RNA probe will be cut by the enzyme. Cleavage of the RNA probe at the site of the mismatch(es), which may be assayed by a number of different means, is thus used to detect the altered DNA sequence. Since RNaseA will cleave free, unhybridized RNA molecules, it is essential for the cleaved fragments to remain hybridized to the target sequence. This makes it impossible for the target DNA sequence to react repeatedly with multiple copies of the probe. An assay having some similar characteristics has recently been described by Duck et al. (1987) EPA 0 227 976. In this case, excess, unhybridized probe is first digested away with an enzyme that will not cleave the probe when bound in the probe:target duplex. An assay is then carried out to detect the remaining molecules of the probe hybridized to the target sequence. Because it is essential for excess, unhybridized probe molecules to be first degraded, the target sequence cannot turnover and react repeatedly in the reaction as in the present invention.

Hull Vary et al. (1986) EPA 0 200 057 has described a system in which hybridization of the target sequence to the probe displaces a third polynucleotide that is bound to the probe. At the end of the hybridization reaction, the displaced polynucleotide is degraded into mononucleotides which are detected. Again in this system, each molecule of the target sequence hybridizes with one and only one copy of the probe. Recycling of the target sequence cannot occur. A method to enhance the rate of nucleic acid hybridization has been described by Zapolski et al. (1985) P.C.T. WO 85/05685. In this procedure, the enzyme RecA and a single stranded DNA binding protein are used to promote the hybridization of the probe to the target sequence. This increases the rate of hybridization, but the reaction is still stoichiometric involving the binding of a single molecule of the probe by each molecule of the target. Turnover of the target sequence enabling it to capture multiple copies of the probe does not occur as in the present invention.

The prior art presented above represents a number of different strategies for labeling probes, carrying out hybridization reactions, and enhancing signal detection. There are as yet, however, no nucleic acid hybridization assay systems in widespread use. Existing methods lack adequate sensitivity for many clinical applications and often involve complex assay procedures difficult to carry out routinely in a clinical laboratory. All of the prior systems involve a stoichiometric or unitary hybridization of the probe to the target sequence, such that each target molecule can capture one an only one molecule of the probe. The present invention makes a fundamental departure from this concept.

The primary objective of the present invention is to provide an improved hybridization assay method in which the target sequence serves as a catalytic cofactor for the cleavage of a complementary, labeled nucleic acid probe. Recycling of the target through the reaction pathway enables it to capture many molecules of the probe, thereby leading to a large increase in the sensitivity of the assay.

Yet a further objective of the present invention is to provide formats, reagents, and assay conditions for such catalytic hybridization amplification (CHA) reactions useful in diagnostic tests.

BRIEF DESCRIPTION OF THE DRAWINGS

FIG. 1 is a schematic illustration of a standard hybridization assay for the detection of a DNA target sequence based on the formation of a stoichiometric (1:1) complex between the target sequence and a complementary, labeled nucleic acid probe. In this case the sample DNA is immobilized on a filter support.

FIG. 3 illustrates the CHA method in a solid support format in which cleavage of the complementary labeled probe attached to the support is mediated by RNaseH.

FIGS. 4A and 4B illustrates a hybridization detection system in which two CHA reactions are coupled to produce an exponential amplification of signal.

FIGS. 5A, 5B, and 5C demonstrates the use of a competition assay to detect a specific RNA sequence with the CHA method.

SUMMARY OF THE INVENTION

Figure 2:
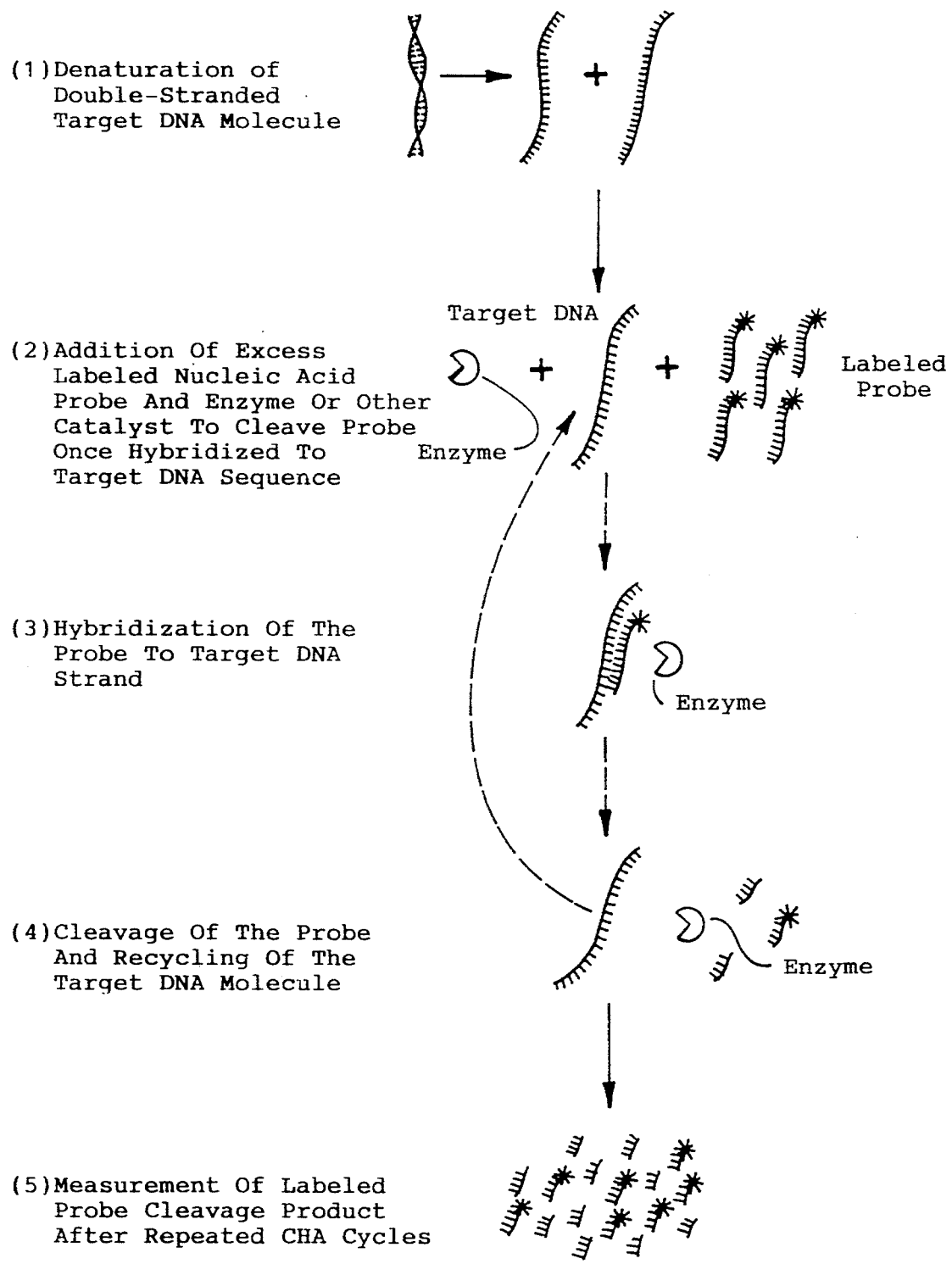
FIG. 2 depicts the use of the CHA method for the detection of a specific DNA sequence. The target DNA sequence serves as a catalytic cofactor for the cleavage of a complementary, labeled nucleic acid probe. Repeated recycling of the target sequence through the reaction (dashed arrow) leads to a large amplification of the signal and enhanced sensitivity compared to standard assay systems based on a stoichiometric or unitary hybridization of the probe to the target sequence.

The present invention of catalytic hybridization amplification (CHA) provides a novel and improved nucleic acid hybridization method useful in diagnostic assays. The target sequence is not detected on the basis of stoichiometric (1:1) hybridization to the probe as in all previous assay systems. The invention concerns the target nucleic acid sequence serving as a highly specific cofactor for a catalytic reaction which leads to the cleavage of a complementary, labeled probe hybridized to the target. Molecules of the probe not hybridized to the target sequence are not cut. Upon cleavage of the labeled probe in the labeled probe:target duplex, the target sequence is released intact and can repeatedly cycle through the reaction pathway. In such assays, cleavage of the probe generates the signal that is detected. The ability of each molecule of the target to capture multiple copies of the probe leads to a large enhancement in the sensitivity of the method. Several embodiments of the CHA method are provided employing simple assay procedures suitable for use in clinical diagnostic tests. Applications of these methods include, but are not limited to, the diagnosis of infectious diseases, genetic defects and cancer. Both single point mutations as well as longer unique sequences can be detected.

DETAILED DESCRIPTION OF THE INVENTION

The invention of catalytic hybridization amplification is unique in that it represents the first example of a non-stoichiometric hybridization process. In such systems the target sequence (either DNA or RNA) serves as a cofactor in a catalytic reaction in which a complementary, labeled nucleic acid probe is cleaved. A generalized version of the CHA method is shown in FIG. 2.

In the first step of the process, the target sequence hybridizes to the probe by the usual rules of base pairing. Once hybridized to the target sequence, the probe is then cleaved into two or more smaller fragments. The cleavage reaction can be catalyzed by an enzyme or occur by other chemical methods. Only molecules of the probe hybridized to the target sequence are cleaved. Excess molecules of the probe not hybridized to the target are not cut. The smaller fragments of the probe generated by the cleavage reaction form less stable duplexes with the target than does the parent molecule, and under conditions of the CHA reaction dissociate from the target. For dissociation to occur rapidly, the melting temperature of the duplexes formed with the smaller fragments should generally be 10° C. or more below the reaction temperature. For short oligonucleotide probes from about 15 to about 35 nucleotides in length, this will occur following a single cleavage near the middle of the probe sequence. For longer probes, which may be up to several thousand nucleotides in length, multiple cleavages must occur, generating fragments shorter than about 35 nucleotides in length, preferably between about 10 and 20 nucleotides long. The target sequence must not be cleaved in the reaction. It is released intact from the probe:target duplex and recycles repeatedly through the reaction pathway. At the completion of the CHA reaction the extent of cleavage of the probe is measured. This generally involves separation of the probe fragment bearing the reporter group label from the intact molecule. It is the cleavage of the probe that signals the presence of the target sequence. Turnover of the target sequence, enabling each molecule to capture and promote the cleavage of many copies of the probe, greatly enhances the sensitivity of the method. Several embodiments of the CHA method will now be described.

In the principal embodiment of this invention, as applied to the detection of a DNA sequence, the cleavage reaction is catalyzed by the enzyme RNaseH, and takes place only when the target DNA sequence is hybridized to a complementary RNA probe, forming an RNA:DNA duplex. RNaseH is highly specific: it will not cut free molecules of the probe that are not hybridized to the target DNA sequence, nor does it cleave the target DNA sequence. Hence, upon cleavage of the probe, the target sequence is released intact and can repeatedly cycle through the reaction pathway as outlined in FIG. 2. A detailed description of the components (probes, labels, etc.), procedures, and conditions for this embodiment of the CHA method follows.

Probes that can be used in the invention range from oligonucleotides of about 15 to about 50 nucleotides in length to longer polynucleotides which may be up to several thousand nucleotides long. A probe of about 15 residues is the shortest sequence that can be used to selectively hybridize to a complementary target sequence (e.g. a unique viral sequence) against the background of human DNA (see Thomas, C. A., Jr. (1966) Progress In Nucleic Research and Molecular Biology 5, 315). More often, sequences of at least 20 to about 25 nucleotides have to be used to assure a high level of specificity. Short oligonucleotides up to about 25 residues are generally labeled with a single reporter group, either near the 5'- or 3'-end of the strand. Longer sequences may be labeled up to a density of about one reporter group per 15 nucleotide residues. The composition of the probe can be entirely RNA. Alternatively, the probe may contain one or more interspersed sequences not cleavable by RNaseH. Such sequences not cleaved by RNaseH can be composed of DNA, or of RNA in which either the phosphate groups or the sugar moieties are modified so as to prevent cleavage by the enzyme. Appropriate modifications of the phosphate groups include, but are not limited to, alkyl or aryl phosphotriesters, hydrogen phosphonates, alkyl or aryl phosphonates, alkyl or aryl phosphoramidates, phosphorothioates, or phosphoroselenates. The preferred modification of the ribose sugar to prevent cleavage by RNaseH is the conversion of the 2'—OH group to an alkyl or aromatic ether. To permit recognition by RNaseH, the cleavable RNA sequence(s) must be at least 3 residues in length.

Probes containing interspersed sequences not cleavable by RNaseH focus the activity of the enzyme to specified regions and are, therefore, preferred. If an oligonucleotide 26 residues in length composed entirely of RNA was used as a probe, cleavage at many sites would be nonproductive, that is, would not lead to release of the target sequence. For example, cleavage of the strand between residues 23 and 24 would generate one fragment 23 residues in length and a second fragment of only-3 residues. The trinucleotide would dissociate from the target sequence very readily, but the 23-mer would form a duplex with the target sequence almost as stable as that formed with the parent molecule, and, hence, would not be released. Alternatively, if the oligonucleotide had the sequence $DNA_{11}$-$RNA_4DNA_{11}$ cleavage would be limited to the central four RNA residues. The longest fragment so generated would be 15 residues. The Tm of this fragment would be about 20° C. to 25° C. below that of the parent 26-mer (see Equation 1) and would readily dissociate from the target sequence under the CHA reaction conditions. Thus, each time the probe was cleaved, the target sequence would be released and able to recycle through the reaction pathway. In the case of the pure RNA oligonucleotide probe two or more cleavages of the probe may be necessary to release the target. For longer probes, the length of the interspersed noncleavable sequences should be less than about 35 nucleotides long and preferable between 10 and 20 nucleotides in length, to permit rapid release of the fragments generated by RNaseH cleavage from the target sequence.

A mixed DNA-RNA-DNA oligonucleotide probe is particularly useful for the detection of single point mutations, as is required for the diagnosis of certain genetic diseases such as sickle cell disease. Consider a probe that forms a perfect duplex with the normal target sequence, and a duplex with the mutant gene in which there is a single base pair mismatch. The entire probe, including the flanking DNA sequences, provides the specificity for the target sequence normally achieved through hybridization. The greatest difference in the stability of the two helices is obtained with a relatively short oligonucleotide probe in which the mismatch is near the middle of the sequence. Even in this case, however, the melting temperature of the perfect duplex formed with the normal sequence is only about 5° C. to 10° C. greater than that for the duplex formed with the mutant sequence having the mismatch. Although it is possible to distinguish the normal from the mutant sequence based on this small difference using a standard hybridization format such as that shown in FIG. 1, the reliability of the method is not sufficient for routine diagnostic use. The CHA reaction scheme, however, affords a further level of specificity that enables these two sequences to be readily differentiated. As noted above, cleave of an DNA-RNA-DNA probe by RNaseH is limited to the central RNA sequence. If the RNA sequence is four or five residues, a single base pair mismatch disrupts the structure of the RNA:DNA duplex sufficiently to prevent cleavage of the RNA strand by RNaseH. Thus, the probe would be cleaved when hybridized to the normal target sequence but not when hybridized to the mutant sequence. Only the normal target sequence would serve as a catalytic cofactor for the cleavage of the probe. If the central RNA sequence is between six and eight residues, two mismatches within the RNA:DNA portion of the duplex may be necessary to disrupt the structure sufficiently to prevent cleavage by RNaseH. This can be accomplished using a probe in which there is a single mismatch with the normal sequence and two mismatches with respect to the mutant sequence, e.g.

... dAdCrArUrCrCrGrArUdAdG ... probe
                  *
... dTdGdTdAdTdGdCdTdAdTdC ... normal target sequence ... dAdCrArUrCrCrGrArUdAdG ... probe
             *         *
... dTdGdTdAdTdGdAdTdAdTdC ... mutant sequence where dN (N=A,C,T or G) is a deoxyribonucleotide (DNA), rN a ribonucleotide (RNA), and * a mismatched base pair.

Probes themselves can be made and modified by both molecular biology and synthetic techniques. Long probes greater than about 60 nucleotides in length are generally synthesized and labeled by enzymatic methods. Long RNA fragments can be synthesized from a DNA template using either SP6 or T7 RNA polymerase. Oligonucleotides are generally synthesized by chemical methods, see "Oligonucleotide Synthesis: A Practical Approach" (Gait, M. J., ed.) IRL Press, Oxford (1984), which is incorporated herein by reference. The phosphoramidite method is the preferred chemistry at present. The synthesis can be carried out with the growing oligonucleotide chain attached to a solid support, such as polystyrene or glass beads, or free in solution. DNA, RNA and DNA-RNA-DNA oligonucleotides can be prepared by these approaches. DNA, RNA and mixed DNA-RNA molecules can also be further ligated together in any combination using the enzyme T4 RNA ligase. Any of the above techniques can be employed for the synthesis of probes useful with this invention.

Radioisotopes, fluorophores, lumiphores (chemiluminescent or biolumeniscent substrates), and enzymes can all be used as reporter groups in catalytic hybridization amplification systems. The fact that the system produces a large amplification response before the actual detection procedure is carried out, in most cases, significantly reduces the demand on the sensitivity of the reporter group being used. Reporters can be chosen for convenience in the assay system, or because they are better adapted to the assay format (instrumentation versus manual procedures), as well as for greatest sensitivity.

Radioisotope such as $^{32}P$, $^{14}C$, $^{120}I$, and tritium can be easily incorporated into DNA and RNA probes with molecular biology techniques, either during synthesis or after completion. Probes synthesized chemically can also be labeled with radioisotopes. While radiolabeling has certain advantages for experimental and research purposes, it does not appear to be the appropriate method for new tests and assays in the clinical laboratory, and is therefore not preferred.

Nonisotopic labels of choice include: (1) fluorophores such as fluorescein, Texas Red, Lucifer Yellow, pyrenes, chelated lanthanides, and phycobiliproteins to name a few; (2) lumiphores such as luminol and derivatives; and (3) enzymes such as alkaline phosphatase, peroxidase, β-galactosidase, and luciferases to name a few. The various enzymes can be used to produce color reactions (alkaline phosphatase, peroxidase), fluorescent products (alkaline phosphatase), and luminescence (luciferase).

Fluorophores and lumiphores can be covalently attached to RNA and DNA sequences by a variety of techniques. In the case of a nucleic acid probe in which the 3'-terminal nucleotide is a ribose residue, the ribose diol at the 3'-end of the sequence can be oxidized with periodate to form a reactive dialdehyde. A reductive alkylation reaction can now be carried out where the dialdehyde can form a Schiff's base with a variety of fluorescent derivatives containing a primary amino group (dansylethylenediamine, N-(1-pyrenesulfonyl)ethylenediamine, 5-((2-aminoethyl)thiouridyl)-fluorescein, etc.). Primary amine derivatives of luminol and other lumiphores can also be coupled. The Schiff's base adducts can be reduced to a stable secondary amine linkage using sodium borohydride or sodium cyanoborohydride. Fluorescent derivatives containing hydrazine groups (fluorescein thiosemicarbazide, Texas Red hydrazide, coumarin hydrazide, Lucifer Yellow CH, etc.) can also be coupled to terminal aldehydes produced by periodate oxidation (see Odom O. W., Jr., et al. (1980) Biochemistry 19, 5947-5954).

In the case of synthetic oligonucleotides, an aliphatic primary amino group can be readily incorporated at the 5'-terminal end of the molecule in several ways. [1] A specially protected phosphoramidite derivative of 5'-amino-5'-deoxythymidine can be incorporated as the final residue (Smith, L. M. et al. (1985) Nucleic Acids Research 13, 2399-2412). Primary amines can also be incorporated into oligonucleotides via special phosphoramidite derivatives, which can also be added at the last step in the synthetic procedure. Two such derivatives are available commercially, one from Applied Biosystems, Inc. (Aminolink 1, Part Number 400498) and one from Chem-Genes, Inc. in which the amino group is protected with the monomethoxytrityl group. Once a primary amine is incorporated

[1] Oligonucleotides are generally synthesized from the 3'-to the 5'-end of the chain. into the oligonucleotide, a number of amine selective fluorescent derivatives (fluorescein-5-isothiocyanate, Texas Red, succinimdyl-1-pyrene butyrate, etc.) can be easily coupled to the primary amine group under mild conditions. Fluorescent lanthanides (Europium, Terbium, etc.) can be incorporated into oligonucleotides by first reacting the primary amine with diethylenetriaminepentacetic acid anhydride to produce a chelator for binding the lanthanides.

Enzyme labels of particular interest include: alkaline phosphatase, peroxidase, β-galactosidase, glucose oxidase, bacterial (FMN/NADPH) luciferases, and insect (ATP) luciferases to mention a few. Other labels include microperoxidases, functionalized heme derivatives, and other metal chelates with catalytic activity. Enzymes can be incorporated into RNA, DNA and mixed RNA-DNA probes using procedures similar to those discussed above for fluorescent derivatives. As an example, alkaline phosphatase can be incorporated into an oligonucleotide probe containing a 5'-terminal primary amine in the following manner. The primary amine containing oligonucleotide is reacted with an excess of the bifunctional reagent disuccinimidyl suberate (DSS is a highly specific reagent for coupling primary amines under mild conditions) to produce the mono adduct with the oligonucleotide. The mono adduct DSS-oligonucleotide can be easily purified. The mono adduct DSS-oligonucleotide is now reacted with alkaline phosphatase under mild conditions. The final product "alkaline phosphatase-DSS-5'-oligonucleotide" is purified by gel filtration and ion-exchange chromatography. The specifics of this coupling procedure are given in Jablonski, E. et al. (1986) Nucleic Acid Research 14, 6115-6128, which is incorporated by reference.

In this first embodiment of the CHA method, RNaseH is responsible for catalyzing the cleavage of the probe once it hybridizes to the target sequence. The enzyme is highly specific; it is a ribonuclease that cleaves only the RNA strand within an RNA:DNA duplex. The enzyme can be obtained from both eukaryotic and bacterial sources. The *E. coli* RNaseH enzyme, used in the examples, is a single polypeptide chain of about 17,500 molecular weight. The enzyme is very stable, the gene for the protein has been cloned and sequenced, and overproducing strains have been constructed which produce the enzyme in large amounts (Kanaya, S. and Crouch, R. J. (1983) Journal of Biological Chemistry 258, 1276-1281. For these reasons, its use is generally preferred. For CHA reactions carried out above a temperature of about 50° C., a more thermostable form of the enzyme is desirable. Such variants of the enzyme may be isolated from thermophilic organisms, or produced by mutagenesis of *E. coli* RNaseH using recombinant DNA techniques (e.g. by the introduction of a suitably positioned disulfide bridge).

The optimal temperature for carrying out the CHA reaction is generally from about 5° C. to about 25° C. below the melting temperature of the probe:target duplex. This provides for a rapid rate of hybridization and high degree of specificity for the target sequence. Consider, for example, a DNA-RNA-DNA probe 26 residues in length in which the G plus C fraction is 50%. At a salt concentration of 0.1 M, the predicted melting temperature of the probe:target duplex, according to Equation 1, is about 55° C. The upper limit for the CHA reaction temperature is, therefore, about 50° C. Cleavage of the probe near the middle of the sequence generates two fragments each of which have melting temperatures of about 25° C. As noted above, for these fragments to dissociate rapidly from the target sequence, the CHA reaction temperature should be at least 10° C. greater than this value, i.e. equal to or greater than 35° C. Hence, the optimal range for the CHA reaction temperature with this probe is from about 35° C. to about 50° C.

The CHA reaction is usually carried out for about 15 minutes to about 1 hour. Generally, each molecule of the target sequence will turnover between 100 and 1000 times in this period, depending on the length and sequence of the probe, and the specific reaction conditions (see Example 1). For each copy of the target sequence present in the test sample 100 to 1000 molecules of the labeled probe will be cleaved by RNaSeH. This level of amplification leads to an enormous increase in sensitivity compared to assays based on a stoichiometric hybridization format. Even higher levels of amplification can be obtained by allowing the CHA reaction to proceed longer.

During the CHA reaction, it is necessary to suppress cleavage of the probe, as well as the target sequence, by nonspecific nucleases. This is important for assays based on standard hybridization formats as well. Such nucleases are generally removed from the sample during the isolation of the DNA by heating or extraction procedures. A number of inhibitors of single-stranded ribonucleases such as vanadate, Inhibitors it-ACE (5 Prime-3 Prime, Inc.) and RNAsin, a placental protein, do not affect the activity of RNaseH. In order to further protect the probe from nonspecific degradation, it is desirable to include such inhibitors during the CHA reaction.

Following the CHA reaction, it is necessary to determine the extent of cleavage of the probe. This is usually accomplished by separating the cleavage products bearing the label from the remaining uncleaved molecules of the probe. Methods for such separation include, but are not limited to:

(1) Electrophoresis of the CHA reaction products to separate the cleaved fragments from molecules of the intact probe on the basis of size.

(2) The use of strong acids, like trichloroacetic acid, to selectively precipitate the relatively large uncleaved labeled probes from the smaller cleaved fragments.

(3) The incorporation of a high affinity label into the probe, in addition to the reporter group, to provide for the separation of the uncleaved probes after the CHA reaction, using an affinity support.

(4) The use of a support material containing a complementary polynucleotide sequence to immobilize the uncleaved labeled probe after the CHA reaction is carried out, leaving the cleaved fragments in solution.

In the first separation method, electrophoresis of the CHA reaction products through a gel matrix is used to separate the cleaved fragments bearing the label from the intact probe. The smaller fragments migrate through the gel more rapidly than the larger intact molecule. For probes up to about 100 nucleotides in length a polyacrylamide gel matrix is generally used. For longer probes, polyacrlamide, agarose or a composite gel made up of these two components is generally preferred. After the separation has been achieved, fragments bearing the reporter group label and the original probe are resolved into separate bands which can be readily localized and quantitated.

The second separation method involving strong acid precipitation is used mainly in those situations in which a long probe (greater than about 50 nucleotides in length) containing either radioisotope or fluorescent labels is cleaved via the CHA process into a number of relatively small labeled fragments (<10 nucleotides in length). Introduction of a strong acid (trichloroacetic, etc.) into the solution causes the intact probe to precipitate, while the smaller cleaved fragments remain in solution. The solution can be centrifuged or filtered to remove the precipitate. The supernatant containing the cleaved labeled fragments can now be quantitated. A more detailed discussion of this method is given in Example 1, below.

The third separation method involves a probe labeled with both a high affinity group and a reporter group, and an affinity support is used to carry out the separation procedure. The probes used in this case can be either an RNA sequence or contain interspersed sequences not cleaved by RNaseH such as a mixed DNA-RNA-DNA sequence. The probe is designed with an affinity label (such as biotin, avidin, lectins, haptens, or antibodies) incorporated at or near one of the terminal positions of the probe. The reporter group label (enzyme, fluorophore, lumiphore or radioisotope) is incorporated at or near the opposite terminal position. (With a long polynucleotide probe, many or all of the interspersed sequences not cleavable by-RNaseH can be labeled with the reporter group). The cleavable portion of the probe sequence, thus, lies between the affinity group and the reporter group. A minimum of about 15 nucleotides is necessary between the two labels, with 20 to 50 nucleotides being more ideal. The same methods as discussed above for incorporating reporter group labels into probes are also used for the attachment of affinity labels. In this separation procedure it is also necessary to have support material which contains a corresponding affinity group which binds specifically and strongly to the affinity label incorporated into the probe. For example, if the affinity label biotin is incorporated into the probe, then the appropriate affinity support material should contain avidin or streptavidin. Many support materials such as glass beads, latex beads, cross-linked dextran (Sepharose) beads, etc. containing covalently linked avidin are commercially available.

After the CHA reaction is carried out, the support material is added to the sample. Molecules of the intact probe bind tightly to the support. Cleaved fragments bearing the reporter group but not the affinity label remain in solution and can be quantitated.

The fourth separation procedure is in principle very similar to that just described, but employs a nucleic acid sequence within the probe not cleaved during the CHA reaction as the affinity label. A complementary nucleic acid sequence is attached to a solid support and serves as a catcher sequence. When the cleavage of the probe during the CHA reaction is mediated by RNaseH, the sequence playing the role as the affinity label can be DNA, or an RNA sequence in which the sugar or phosphate groups are modified to prevent cleavage by RNaseH. The affinity label sequence is separated from the reporter group by a portion of the probe cleaved by RNaseH during the CHA reaction, for example 5'-DNA-RNA-DNA-(reporter group)

in which case the DNA sequence at the 5'-end of the probe, or a portion thereof, serves as the affinity label. An affinity label sequence o 20 to 50 nucleotides in length is most ideal, but longer sequences can also be used. Sequences less than 15 nucleotides are least useful. A portion of the affinity label sequence can be complementary to the target sequence or it can be a separate appendage attached to the probe. The latter is preferred because a generalized catcher sequence can then be used. In this case one set of catcher beads can be used with many different target specific probes.

A number of different chemical methods may be used to attach the catcher sequence to a solid support, see for example, Gilham, P. T. (1971) Methods of Enzymology, Vol. 21 (Grossman, L. and Moldave, K., eds.) pp. 191–197, Academic Press, New York; Potuzak, H. and Dean, P. D. G. (1978) Nucleic Acids Research 5, 297–303; Robertson, D. L. and Davidson, N. (1972) Biochemistry 11, 533–537; and Moss, L. G. et al. (1981) Journal of Biological Chemistry 256, 12655–12658, which are incorporated herein by reference. It is also possible to synthesize the catcher sequence directly on the solid support which later will be used in the assay. As noted above, oligonucleotides are generally synthesized from the 3'- to the 5'-end of the chain. If the synthesis is carried out on a solid support, the first nucleotide from the 3'-terminal end is generally attached to the support via its 3'-hydroxyl group through an ester linkage. Conditions required to remove protecting groups on the nucleotide bases (treatment with concentrated ammonia at 55° C. for 6 to 10 hours) cleave this linkage readily. If the oligonucleotide is to remain bound to the support the linkage to the 3'-hydroxyl group must be changed to one not cleaved under these conditions. Suitable functional groups through which the 3'-OH may be attached include ether linkages, phosphate triesters, phosphate diesters and aromatic carbamates. The functional group preferred for simplicity synthesis is a $\beta$-cyanoethyl phosphtriester. The attachment is accomplished by the reaction of a 3'-$\beta$-cyanoethyl-N,N-diisopropyl phosphoramidite derivative of the first nucleotide (available commercially for all four bases) to a solid support containing free OH groups. Such supports can be prepared from a variety of materials including glass, polystyrene, latex or cross-linked dextran (Sepharose) beads, cellulose, or nylon or teflon membranes. After the first nucleotide is attached to the support, the remaining sequence is synthesized by the normal phosphoramidite method. At the culmination of the synthesis, the deblocking procedures convert the $\beta$-cyanolethyl phosphotriester to a phosphodiester through which the oligonucleotide remains linked to the support. After a support material is prepared by any of the above procedures, the attached oligonucleotide can be extended, if desired, by a number of different enzymatic methods, thereby yielding longer nucleotide sequences bound to the support. Suitable procedures include, but are not limited to, addition of nucleotide residues to the fragment with DNA polymerase or terminal transferase, and ligation of polynucleotides to the initial sequence attached to the support using DNA or RNA ligase.

In each of the four separation methods just described, the CHA reaction is first carried out in solution. Alternatively, the labeled probe may be attached to a solid support, in which case cleavage of the probe during the CHA reaction releases fragments bearing the reporter group into solution (see FIG. 3). The major advantage of the is approach is the relative ease of the separation step after the CHA reaction is completed: the solid support material containing remaining molecules of the intact probe are simply removed from the sample by physical means such as filtration or centrifugation; the cleaved fragments bearing the reporter group are left in solution and can be quantitated. Suitable solid support materials include glass, polystyrene, latex or cross-linked dextran (Sepharose) beads, cellulose, or nylon or teflon membranes. Magnetized beads can also be used, in which case the beads are separated from the solution by the application of a magnetic field. The probe can be attached to the solid support either through a covalent or a noncovalent (e.g. biotinavidin) linkage. A covalent linkage is preferred because ore its greater stability. Suitable procedures for covalently attaching nucleotide sequences to solid supports by both chemical and enzymatic methods are described in the preceding paragraph.

When using the solid support CHA method, it is desirable to fist cut the sample DNA into smaller fragments so that the target sequence can readily diffuse to the surface of the bead to hybridize with the bound probe. This can be accomplished by shearing the DNA through mechanical forces (e.g. sonication) or by cleaving the DNA at specific sites using a restriction enzyme. Alternatively, a small fragment containing the target sequence can be synthesized with DNA polymerase using the sample DNA as a template. In this procedure an oligonucleotide used as a primer is first hybridized to the sample DNA upstream (i.e. 5') from the target sequence. The primer is then extended across the target sequence (copying the complementary strand) using DNA polymerase. The product:

5'-Primer-Target Sequence is then brought into the CHA reaction. It is also possible to repeat the reaction with DNA polymerase a number of times to increase the number of copies of the target sequence. Such a procedure is carried out in the so-called polymerase chain reaction (Mullis, K. B. et al. (1986) EPA O 200 362; and Mullis, K. B. (1986) EPA O 201 184). Since target amplification and the CHA method involve entirely separate steps in the assay procedure the two can be used in combination. This can be useful to detect a nucleic acid sequence present originally in the sample in extremely low copy number. For most diagnostic applications, however, the high degree of sensitivity of the CHA method alone is sufficient.

All of the above discussions on the use of the CHA method have centered around the detection of DNA target sequences. In some cases, it may be advantageous to detect RNA target sequences, such as ribosomal RNA sequences. This can be readily accomplished with any of the above CHA reaction procedures utilizing RNaseH by first synthesizing a complementary DNA (cDNA) copy of the original RNA sequence with the enzyme reverse transcriptase. In this procedure, an oligodeoxynucleotide primer is first hybridized to the sample RNA upstream (i.e. 5') of the target sequence. With the addition of reverse transcriptase and the four deoxynucleotide triphosphates (A, G, T and C), the primer is extended producing a cDNA copy of the target RNA. The product:

5'-Primer-cDNA Target Sequence now forms the substrate for the CHA reaction. For a more detailed description of protocols for the use of reverse transcriptase see Maniatis, T., Fritsch, E. F., and Sambrook, J., *Molecular Cloning: A Laboratory Manual,* Cold Spring Harbor Laboratory, New York, pp. 128-132, 1982, which is incorporated herein by reference.

A second embodiment of the CHA method will now be described in which a phosphorothioate derivative of the target sequence is used as the substrate and a complementary labeled DNA probe is cleaved by a restriction enzyme.

Restriction enzymes recognize a specific DNA sequence, generally 4 to 6 nucleotides in length, and cut both strands of the DNA duplex at that site. Several hundred of these enzymes are now known with many different recognition sequences. These enzymes generally cannot be used with the CHA met, hod since the target sequence, as well as the probe, would be cut, and therefore would be unable to recycle through the reaction pathway. However, if the phosphate groups of one of the two strands of a DNA duplex are phosphorothioates, rather than normal phosphate diesters, many restriction enzymes (e.g. Ava I, Ava II, Ban II, Hind II, Nci I, Pst I, and Pvu I) will cleave only the unmodified strand (Taylor, J. W. et al. (1985) Nucleic Acids Research 13, 8749-8764). The phosphorothioate sequence is not cut and hence can serve as a catalytic cofactor for cleavage of a complementary, labeled probe by a restriction enzyme. The target sequence to be used in such an assay must of course contain the recognition site for the restriction enzyme. The modified DNA sequence is prepared from a DNA template using DNA polymerase. If the sample is RNA, reverse transcriptase is used. These reactions are carried out as described above, except that deoxynucleotide α-thiotriphosphates are used as substrates instead of the normal deoxynucleotide triphosphates. All four of the deoxynucleotide α-thiotriphosphates are available commercially. Once the modified target sequence is prepared, the CHA reaction can be carried out using any of the assay formats described above. The same methods for synthesis and labeling of the probe are also applicable. Modified DNA or RNA sequences can be incorporated within the probe flanking the restriction enzyme site, but the recognition site itself must be composed of DNA.

All of the various embodiments and formats of the CHA method described thus far provide a linear amplification of the signal. Since the concentration of the target sequence remains constant, the velocity of the reaction remains unchanged, and the number of molecules of the labeled probe that are cleaved increases linearly with time (see Example 1). As mentioned above, the turnover number, i.e. the number of molecules of the probe cleaved per target sequence per hour, generally ranges between 100 and 1000.

CHA reactions can also be carried out in novel manners that produce an exponential amplification, and therefore, offer an even greater sensitivity. In general, an exponential response is achieved by coupling two or more CHA reactions so as to produce additional copies of the target sequence. A number of different exponential CHA formats can be designed. One version of an exponential CHA format is shown in FIG. 4. In this case, two sets of probe sequences are immobilized on solid supports. The first probe sequence on support I contains a cleavable sequence (T') complementary to the original target sequence, and a non-cleavable sequence (X). The sequence (X) is complementary to a cleavable sequence (X') immobilized on support II. In the first step of the process, target DNA from the sample hybridizes to the complementary cleavable sequence (T') on support I. Once hybridized to the target sequence, (T') is cut, releasing the sequence (X) from the support. (X) then diffuses from the support and hybridizes with the cleavable sequence (X') on support II. This cannot occur until (X) is released from the support. Sequences (X) and (X') while immobilized on two separate macroscopic supports cannot hybridize with one another. Once the duplex between (X) and (X') is formed, (X') is cleaved. This releases a second copy of the target sequence which can in turn react with support I and further propagate the reaction. Thus, one cycle of the CHA reaction yields two copies of the target sequence; the second cycle yields four copies of the target sequence; the third cycle yields eight copies; etc. In the configuration shown, one reporter group label is released from support II for each molecule of target that is generated in the reaction. It can be shown that the amount of the free label released from support II is given by the following formula:

$$L = (A/2)X(e^{kt} + e^{-kt}) - A \qquad (2)$$

where A is the initial number of copies of the target present in the sample, k is the square root of the product of the turnover numbers for the two separate CHA reactions, and t is time. The first term of the expression $(A/2 \times e^{kt})$ rapidly becomes dominant. The amount of free label increases exponentially with time, conferring an extremely high degree of sensitivity to the assay. If the turnover number for each of the CHA reactions is only 1 per minute, a single copy of the target sequence will cause $2.4 \times 10^8$ labels to be released into solution within 20 minutes. This number can be easily detected with simple fluorescent or enzyme labeling groups. Turnover numbers much greater than 1 per minute can be achieved (see Example 1). Coupled CHA assay systems, thus, provide the capability for single copy target detection with a reaction time of only a few minutes.

Finally, we describe a competition assay based on the CHA method to detect an RNA target sequence. In this case, both a DNA molecule and a labeled probe are added to the sample to be analyzed (FIG. 5). The probe sequence (A') may be composed entirely of RNA or contain interspersed sequences that cannot be cleaved by RNaseH. The DNA fragment contains within it a sequence (A) complementary to the labeled probe. In the example shown, the central portion of the probe is RNA, and it is flanked on either side by DNA sequences. The RNA:DNA duplex formed when (A) and (A') hybridize together forms a substrate for RNaseH. RNaseH can cleave the labeled probe, releasing the DNA fragment intact which serves as a catalyst to further propagate the reaction. This would occur if the target RNA sequence were not present within the sample (FIG. 5b). If the target RNA sequence were present, this reaction would be inhibited (FIG. 5a). The target sequence contains the sequence (A'), as well as an adjacent sequence (B') further complementary to the DNA fragment. The DNA fragment thus forms a more stable duplex with the target sequence than with the probe. This enables the target molecule to compete very effectively for the binding of the DNA fragment, and thereby blocks the cleavage of the labeled probe by RNaseH (FIG. 5a). This competitive inhibition of the cleavage of the labeled probe is the basis for the assay. The sensitivity of the method may be further enhanced by preventing the RNA—DNA duplex formed with the target sequence from being degraded by RNaseH. This may be accomplished by suitably modifying the DNA fragment. We have found that a variety of modifications of the phosphate backbone of the DNA strand will prevent cleavage of the complementary RNA strand by RNaseH. Such modifications include, but are not limited to, substitution of the normal phosphate diesters with alkyl or aryl phosphotriesters, or with alkyl or aryl phosphonates. These modifications would be incorporated into the DNA molecule used in the assay throughout region B, and in all of region A except for that portion which hybridizes to the central RNA sequence of the probe. If this unmodified sequence within region A is precisely complementary to the RNA sequence within the probe, but contains one or more mismatches with respect to the target sequence, only the probe will be cleaved by RNaseH. The mismatch(es) within the duplex formed between the DNA strand and the target molecule disrupt the helix, thereby, preventing cleavage of the target strand within this region by RNaseH. Cleavage of the target strand elsewhere is prevented by the modifications introduced into the phosphate backbone of the DNA molecule. The mismatch(es) would decrease the stability of the duplex formed between the target sequence and the DNA molecule somewhat, but, due to the additional sequence complementary in region B, the stability of the duplex would remain much greater than that formed with the labeled probe.

The following examples are offered to further illustrate, but not limit, the process, product and techniques of the invention and serve to establish the unique features of the invention which form the basis of its utility.

EXAMPLE 1

Demonstration of Catalytic Hybridization Amplification Mediated by RNaseH

The following example demonstrates the principle of the catalytic hybridization amplification method. The target sequence in this case was oligodeoxythymidylic acid of 12 to 18 nucleotide residues in length (oligo $dT_{12-18}$, purchased from Pharmacia). The molecule serving as the probe was polyriboadenosine labeled with tritium (Amersham). The specific activity of the poly rA used in the study was 574 mCi/nucleotide residue; the chain length varied from about 40 to 140 residues. In the presence of the target sequence, RNaseH catalyzes the cleavage of the labeled poly rA probe. Oligo dT is then released from the duplex intact and recycles repeatedly through the reaction as outlined in FIG. 2.

Cleavage of the poly rA probe catalyzed by RNaseH was compared under three conditions: in the absence of oligo dT; with an equivalent concentration of oligo dT (based on nucleotide residues); and in the presence of 1/1000 the concentration of oligo dT. Each reaction was conducted in a final volume of 100 μl containing 44 picamoles of poly rA (by nucleotide units), 50 mM Tris-HCl buffer pH 8.0, 20 mM KCl, 9 mM $MgCl_2$, 1 mM 2-mercaptoethanol and 25 ug of bovine serum albumin. The reaction was initiated by the addition of 2.3 units of E. coli RNaseH (Bethesda Research Laboratories) and was maintained at 30° C. Aliquots of the reaction mixture were removed at 30 minutes and added to 0.2 ml of a Carrier DNA solution (0.5 mg/ml of salmon sperm DNA, 0.1 M sodium pyrophosphate and 1 mM ethylenediamine tetraacetic acid) and 0.3 ml of 10% trichloroacetic acid. Trichloroacetic acid causes the precipitation of higher molecular weight nucleic acids over about 10 nucleotides in length. Smaller cleavage products, i.e. mononucleotides and short oligonucleotides, remain in solution. After incubation of the samples on ice for 20 minutes, the precipitated nucleic acids were pelleted by centrifugation at $16,000 \times g$ for 15 minutes. The supernatants containing the cleaved fragments were carefully removed, mixed with scintillation cocktail and counted for radioactivity.

In the control sample without oligo dT, less than 0.5% of the poly rA was cleaved in the course of 90 minutes. In the presence of an equivalent concentration of oligo dT nearly 100% of the poly rA was cleaved to trichloroacetic acid soluble fragments within 30 minutes. Cleavage of poly rA in the presence of 1/1000 the amount of oligo dT was linear over 90 minutes, at which time 21% of the poly rA was cleaved to trichloroacetic acid soluble fragments. Since oligo dT was present in a concentration sufficient to hybridize to only 0.1% of the poly rA sequence, each molecule of the oligo dT must have recycled through the reaction, on average, at least: 210 times (2.3 times/minute). Since cleavage of the poly rA strand is in some cases nonproductive, i.e. does not lead to the release of labeled fragments small enough to remain in solution in the presence of trichloroacetic acid, the true turnover number must be even higher. In diagnostic tests based on the CHA method, turnover numbers exceeding 100/hour provide a great enhancement in sensitivity compared to assays based on a stoichiometric hybridization format.

EXAMPLE 2

Site-Specific Cleavage of β-Globin mRNA by RNaseH in the Presence of a Complementary DNA Target Sequence The following is an important example in which the specificity of strand cleavage by RNaseH is clearly demonstrated. RNaseH was shown to cleave β-Globin mRNA at one unique site when a mixture of both α- and β-globin mRNAs was hybridized to a short 25-residue DNA target sequence complementary to a portion of the β-globin mRNA.

The oligodeoxynucleotide 5'-TGTCCAAGT-GATTCAGGCCATCGTT (CODMB-25) was synthesized by the phosphoramidite method using a Beckman automated DNA synthesizer. It is complementary to the nucleotide sequence of mouse β-globin mRNA from residue 269 to 293. Mouse globin mRNA was isolated from reticulocytes obtained from mice rendered anemic by treatment with phenylhydrazine as described by Goosens and Kan (Methods in Enzymology (Antonini, E., Rossi-Bernardi, L. and Chiancone, E., eds.) Vol. 76, pp. 805–817, 1981). Two micrograms of the RNA was added to 1.0 nanomoles of CODMB-25 in a final volume of 25 microliters-containing 10 mM Tris-HCl buffer at pH 7.5, 5 mM $MgCl_2$, 25 mM NaCl and 1 mM dithiothreitol. The concentration of the oligonucleotide is approximately 100-fold greater than the mRNA on a molar basis. The reaction was initiated by the addition of 2 units of E. coli RNaseH, and allowed to proceed for 30 minutes at 37° C. The reaction was stopped by extraction of the sample with a 1:1 mixture (volume:volume) of chloroform and phenol. The RNA species remaining after digestion with RNaseH were then isolated by precipitation with ethanol and analyzed on Northern blots.

The RNA samples were reacted with 1M glyoxal in a 1:1 volume/volume mixture of 10 mM sodium phosphate buffer at pH 6.5 and dimethylsulfoxide for 1 hour at 50° C., and then electrophoresed on a 1.5% agarose gel. The RNAs were transferred from the gel to a Gene Screen Plus filter (DuPont-NEN) by capillary blotting according to the method described by the manufacturer. Prehybridization of the filter was done in 1% sodium dodecylsulfate, 1M NaCl, 10% dextran sulfate, 50 mM sodium phosphate pH 6.5 for 2 hours at 35° C. The filter was then hybridized with either an α- or β-globin specific oligonucleotide probe. The probes were 25 residues in length and hybridize to the very 5'-end of the respective RNAs. Hybridization was conducted in 5 ml of the prehybridization buffer containing 200 microgram/ml denatured salmon sperm DNA plus $2 \times 10^6$ counts/min of the probe, radiolabeled with $^{32}p$ at the 5'-end of the molecule, for 24 hours at 35° C. After the hybridization, the filter was washed in the following order: once in 2X SSC (1X SSC=0.15M NaCl, 0.015M sodium nitrate) for 5 minutes at room temperature, twice in 2X SSC plus 1% sodium dodecylsulfate for 30 minutes at 35° C. and once in 0.1X SSC for 5 minutes at room temperature. The filter was blotted dry and exposed to Kodak XAR-5 film for autoradiography.

In the absence of oligonucleotide, no cleavage of either α- or β-globin mRNA occurred during the reaction with RNaseH. The α- or β-globin specific probes each hybridized to a single band on the Northern blots corresponding to the full length mRNA. The reaction in the presence of CODMB-25 resulted in essentially complete cleavage of the β-globin mRNA. The size of the cleavage product detected with the 5'-β-globin specific probe was exactly that predicted for scission of the mRNA at the site of the RNA:DNA duplex., i.e. 280±20 nucleotides. No other cleavage products were observed. In addition, no cleavage of the α-globin mRNA was evident using the α-globin specific oligonucleotide probe. RNaseH, thus, has the requisite specificity for use in diagnostic tests based on the CHA method. An RNA sequence used as probe will be cleaved by the enzyme if, and only if, it encounters the complementary target DNA sequence within the sample; and free single stranded molecules of the probe not hybridized to the target sequence will not be cut.

EXAMPLE 3

Detection of Cytomegalovirus Using a CHA Method

Cytomegalovirus (CMV) is a large double-stranded DNA virus. Infection with CMV is clinically very important in immunocompromised patients. It is the most prevalent serious infectious disease complication following renal transplantation.

The following illustrates the use of the CHA method to detect CMV. The probe used is a CMV specific sequence 25 nucleotides in length derived from the major immediate early gene:

5'-TCTTGGCAGAGGACTCCATCGTGTC

The central six residues are RNA; the flanking sequences are composed of DNA. The probe is linked to latex beads at the 3'-end of the sequence. Alkaline phosphatase is attached at the 5'-terminal position. DNA is isolated from blood, urine and sputum samples obtained from the patient. The assay for CMV in each of these samples is carried out by the CHA method shown in FIG. 3. Cleavage of the labeled probe is mediated by E. coli RNaseH (5 units/100 microliters). The CHA reaction is carried out for a period of 45 minutes at a temperature of about 40° C. RNasin (50 units/100 microliters) is added to the reaction mixture to suppress nonspecific cleavage of the probe. If CMV is present within the sample, the target sequence will hybridize to the probe, and the probe will be cleaved by RNaseH. Repeated cycling of the target sequence through the reaction pathway enables each copy of the target sequence to capture and promote the cleavage of many molecules of the labeled probe. Following the CHA reaction, the extent of cleavage of the probe is quantitated by measuring the amount of the reporter group, i.e. alkaline phosphatase, released into solution. The beads are first removed from the sample by filtration or centrifugation. The alkaline phosphatase label on the probe fragments in solution is then measured using either a colorimetric or fluorescent producing reagent detection system. The enzyme can be assayed spectrophotometrically at 405 nm by following the hydrolysis of the substrate p-nitrophenyl phosphate to the colored product p-nitrophenol at pH 8.5. Alternatively, the enzyme can be measured fluorometrically using the substrate 4-methylumbelliferyl phosphate. The fluorescent excitation and emission wavelengths used for the assay are 363 nm and 447 nm, respectively. The final color or fluorescent signal provides a measure of the amount of CMV present in the original sample.

In summary, the results of the studies presented demonstrate the utility of the CHA method as a means for the detection of specific nucleic acid sequences. In such assay systems, the target sequence serves as a cofactor for a catalytic reaction in which a complementary, labeled nucleic acid probe is cleaved. Each molecule of the target sequence is thus able to capture and promote the cleavage of multiple copies of the probe. This results in a large increase in the level of sensitivity of the method compared to current diagnostic tests, all of which are based on a stiochiometric hybridization reaction in which the target sequence is able to bind one, and only one, molecule of the probe. As in the examples described, cleavage of the probe must occur only when hybridized to the target sequence. The target sequence is then released from the duplex intact and repeatedly recycles through the reaction pathway. Formats are provided for use of the CHA method in both direct and competition assays. In general, a detection system based on a single CHA reaction provides a linear amplification of signal with time. By coupling two or more CHA reactions together in an appropriate manner, an exponential amplification of signal can be achieved, giving rise to an even greater level of sensitivity.

It therefore can be seen that the invention accomplishes all of the objectives heretofore stated.

What is claimed is:

1. A method of detecting the presence of a target nucleic acid target sequence through hybridization with a substantially complementary labeled nucleic acid probe in which the probe:target nucleic acid sequence ratio is amplified through recycling of the target nucleic acid sequence, said method comprising:
   (a) hybridizing of said target nucleic acid sequence to a labeled nucleic acid probe to provide a probe:target nucleic acid sequence duplex;
   (b) cleaving only the labeled probe within the probe:target nucleic acid sequence duplex with an enzyme which causes selective probe cleavage resulting in duplex disassociation, leaving the target sequence intact;
   (c) recycling of the target nucleic acid sequence by repeating steps (a) and (b); and
   (d) detecting cleaved labeled probe, and thereby determining the presence of said target nucleic acid sequence.

2. The method of claim 1 wherein said cleaving of said labeled probe occurs at a temperature at which molecules weakly bound to sequences other than the target sequence do not remain hybridized.

3. The method of claim 2 wherein said temperature is from about 5° C. to about 25° C. below the melting temperature of the probe:target duplex.

4. The method of claim 2 wherein cleaved and unhybridized probe remains in solution.

5. The method of claim 1 wherein said nucleic acid probe is labeled with a reporter group to permit detection.

6. The method of claim 1 wherein said labeled probe is an oligonucleotide of from about 15 nucleotides to about 50 nucleotides in length.

7. The method of claim 1 wherein said enzyme will cleave only RNA hybridized in a RNA:DNA duplex and will not cleave, the target nucleic acid sequence.

8. The method of claim 1 wherein said labeled nucleic acid probe is composed entirely of RNA.

9. The method of claim 7 wherein said labeled nucleic acid probe contains one or more interspersed sequences that are not cleavable by said enzyme.

10. The method of claim 9 wherein said interspersed sequences are composed of DNA.

11. The method of claim 9 wherein said interspersed sequences are composed of nucleotide residues selected from the group consisting of phosphonates, phosphotriesters, phosphoroamidates and 2'—O alkyl and aryl ribonucleotide.

12. The method of claim 9 wherein RNA sequences within the probe cleavable by said enzyme vary from about 3 to about 15 nucleotides in length.

13. The method of claim 1 in which nonspecific cleavage of the labeled probe is suppressed by the use of single-stranded ribonuclease inhibitors selected from the group consisting of vanadate, RNAsin, and Inhibit-ACE.

14. The method of claim 14 wherein said enzyme is RNaseH.

15. The method of claim 83 wherein said RNAaseH enzyme is obtained from *E. coli*.

16. The method of claim 14 wherein steps (a) through (c) are carried out at a temperature above 50°.

17. The method of claim 1 wherein said detecting of cleaved probe is accomplished by separating cleavage products bearing the label from uncleaved molecules of probe remaining in solution.

18. The method of claim 17 wherein separation of cleavage products is determined by electrophoretic separation of cleavage products beating the label from uncleaved molecules of probe.

19. The method of claim 17 wherein the separation of cleavage products is determined by using strong acids to selectively precipitate uncleaved molecules of the probe, leaving cleavage products beating the label in solution.

20. The method of claim 17 wherein separation of cleavage products is accomplished with a probe modified with both an affinity label and a reporter group, and in which a solid support to which a corresponding affinity group is attached is used to adsorb molecules of intact probe, leaving cleaved fragments bearing the label in solution, said method comprising the additional steps of:
   adding solid support material following the hybridizing and cleaving steps;
   associating the affinity label attached to the probe with the corresponding affinity group on the solid support;
   separating the solid support from the solution containing the cleaved fragments of the probe bearing the reporter group; and
   detection of the reporter groups in solution.

21. The method of claim 20 in which said solid support is selected from the group consisting of polystyrene, cross-linked dextran or glass beads, cellulose, and a teflon or nylon membrane.

22. The method of claim 21 in which said solid support is magnetized and the solid support is separated from the bulk solution by the application of a magnetic field.

23. The method of claim 20 wherein said separation of cleavage products is accomplished with a nucleic acid affinity label and the corresponding affinity group attached to the solid support is a complementary nucleic acid sequence.

24. The method of claim 1 wherein said labeled probe is attached to a solid support during the steps of hybridization and cleavage, and cleaved fragments beating the label are released into solution.

25. The method of claim 24 in which said solid support is selected from the groups consisting of polystyrene, cross-linked dextran or glass beads, cellulose, and a teflon or nylon membrane.

26. The method of claim 25 in which said solid support is magnetized, and the solid support is separated from solution by application of a magnetic field.

27. The method of claim 1 for detection of a nucleic acid sequence in which the target is first used as a template for synthesis of a complementary DNA copy of the target sequence said method comprising:

hybridizing of a primer to a target nucleic acid sequence 3' to the target sequence;

extending of the primer with a DNA polymerase across the target sequence to produce a complementary DNA copy of the target sequence; and detecting the complementary DNA copy of the target sequence according to the method of claim 1.

28. The method of claim 97 wherein the complementary DNA copy of the target sequence contains phosphorothioates.

29. The method of claim 28 wherein said enzyme will cleave only RNA hybridized in an RNA:DNA duplex and will not cleave the complementary target sequence.

30. The method of claim 14 wherein said RNaseH is isolated from a thermophilic organism.

* * * * *

UNITED STATES PATENT AND TRADEMARK OFFICE
CERTIFICATE OF CORRECTION

PATENT NO. : 5,403,711
DATED : April 4, 1995
INVENTOR(S) : Joseph A. Walder and Roxanne Y. Walder It is certified that error appears in the above-indentified patent and that said Letters Patent is hereby corrected as shown below:

In column 21, claim 1, line 30, after "acid" delete "target".

In column 21, claim 7, line 66, after "cleave" delete ",".

In column 22, claim 14, line 19, delete "14" and substitute therefor --7--.

In column 22, claim 15, line 21, delete "83" and substitute therefore --14--.

In column 22, claim 19, line 37, delete "beating" and substitute therefor --bearing--.

In column 23, claim 24, line 3, delete "beating" and substitute therefor --bearing--.

In column 23, claim 27, line 16, after "sequence" insert --,--.

In column 24, claim 28, line 8, delete "97" and substitute therefor --27--.

Signed and Sealed this

Twenty-third Day of January, 1996

Attest:

BRUCE LEHMAN

*Attesting Officer*     *Commissioner of Patents and Trademarks*